Figure 1:
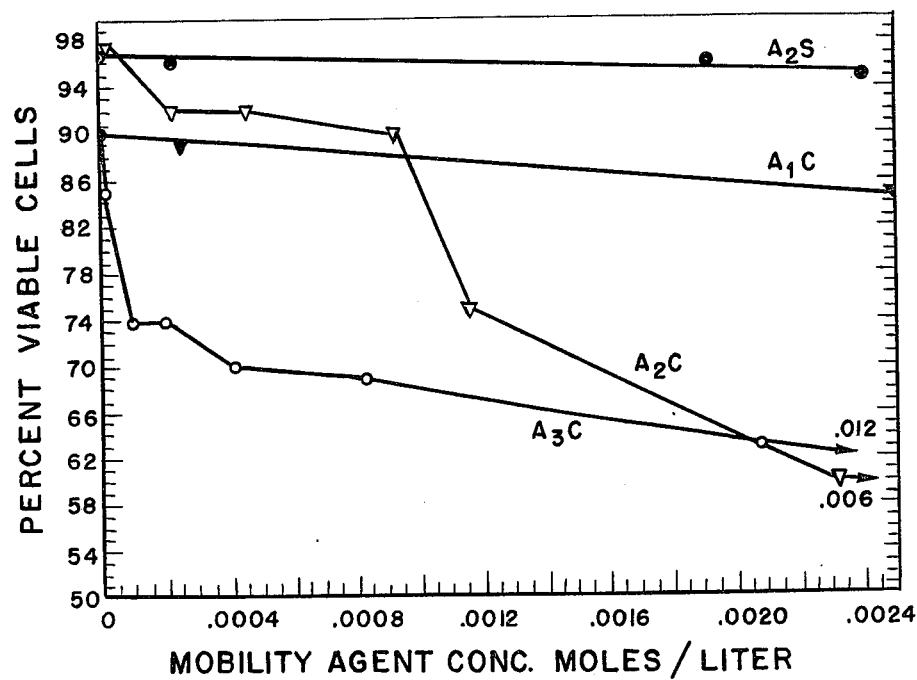

United States Patent [19]

Kosower et al.

[11] 4,001,428
[45] Jan. 4, 1977

[54] CYCLOPROPANE DERIVATIVES AND USE THEREOF AS CELL MEMBRANE MOBILITY AGENTS

[75] Inventors: Edward M. Kosower; Nechama S. Kosower, both of Tel-Aviv, Israel

[73] Assignee: Polymer Sciences Corporation, New York, N.Y.

[22] Filed: July 22, 1975

[21] Appl. No.: 598,133

[30] Foreign Application Priority Data

July 22, 1974 Israel .................................. 45320

[52] U.S. Cl. .............................. 424/307; 195/1.8; 260/468 H
[51] Int. Cl.² .................. A61K 31/25; C12K 9/00; C07C 69/00
[58] Field of Search ................ 260/468 H; 195/1.8; 424/307

[56] References Cited

UNITED STATES PATENTS

| | | | |
|---|---|---|---|
| 3,737,450 | 6/1973 | Henrick et al. | 260/468 H |
| 3,792,079 | 2/1974 | D'Orazio | 260/468 H |
| 3,925,461 | 12/1975 | Henrick et al. | 424/307 |

*Primary Examiner*—Sam Rosen
*Attorney, Agent, or Firm*—Pennie & Edmonds

[57] ABSTRACT

Compounds capable of functioning as membrane mobility agents in plant and animal cells are described. These compounds have a structure represented by the formula

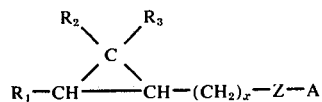

in which A represents a hydrophilic chain; Z represents either an ester linkage

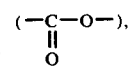

an amide linkage

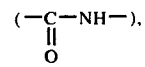

or an ether linkage (—O—); $R_1$ represents either a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

The membrane mobility agents of the invention promote the lateral mobility through cell membranes of molecules ranging in size from phospholipids to surface antigens. They represent a new class of biologically active molecules which may be used to alter the mobility of membrane components in animal and plant cells to alter such cells in their response to external stimuli. Among their uses are altering the immunological response of lymphocytes; altering the pharmacological response of target cells; altering the biological properties of cancer cells; and fusing two or more cells to create a new hybrid cell containing the genetic information from the fused cells.

16 Claims, 4 Drawing Figures

CYCLOPROPANE DERIVATIVES AND USE THEREOF AS CELL MEMBRANE MOBILITY AGENTS

BACKGROUND OF THE INVENTION

Molecules ranging in size from phospholipids to surface antigens move laterally through cell membranes, facts conveniently represented by the fluid mosaic model formulated by Singer and Nicholson, *Science*, 175, 720–731 (1972). Molecular mobility rises with increasing membrane fluidity [cf/ Shimshick et al. *J. Supramol. Biol.*, 1, 285–289 (1973); Michaelson et al., *Biochemistry*, 12, 2637–2645 (1973); and Pagano et al., *Science*, 181, 557–559 (1973)], which, in turn, is related to the proportion of unsaturated alkanoic acid residues present in both natural [Fox et al., *Membrane Molecular Biology* (1972)] and bilayer model [Sackman et al., *J. Am. Chem. Soc.*, 94, 4482–4498 (1972)] membranes. There is scattered evidence in the literature showing that assembly of membrane transport systems [Tsukagoshi et al., *Biochemistry*, 12, 2816–2829 (1973)] and the membrane functions of transport [Schairer et al., *J. Mol. Biol.*, 44, 209–214 (1969); Esfahani et al., *Proc. Natl. Acad. Sci. U.S.*, 68, 3180–3184 (1971); and Linden et al., *Proc. Natl. Acad. Sci. U.S.* 70, 2271–2275 (1973)] and permeability [de Kruyf et al., *Biochim. Biophys. Acta*, 298, 479–499 (1973)] are augmented with increased membrane fluidity [McConnell et al., *Biochem. Biophys. Res. Commun.*, 47, 273–281 (1972)]. Logic therefore dictates that agents which increase membrane fluidity might produce useful and interesting biological changes.

STATEMENT OF THE INVENTION

During an intensive study of membrane fluidity, we discovered a new class of biologically active compounds which promote the lateral mobility of fluorescent antibody-labeled antigenic sites through lympocyte membranes. These compounds, which may be termed "membrane mobility agents," are capable of altering the mobility of membrane components in animal and plant cells to biologically alter such cells in their response to external stimuli. Structurally, the membrane mobility agents of the invention are characterized by the formula 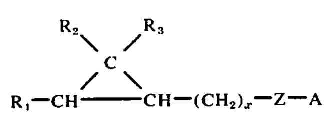 in which A represents a hydrophilic chain; Z represents either an ester linkage an amide linkage or an ether linkage (—O—); $R_1$ represents either a straight-chain alkyl group or a straight-chain alkyl group interrupted by one or more cyclopropyl groups; $R_2$ and $R_3$ each represent either hydrogen lower alkyl, or a halogen group; and $x$ represents an integer from 2 to 10.

Among the most effective of such compounds are the cyclopropane fatty acid esters having a structure represented by the formula 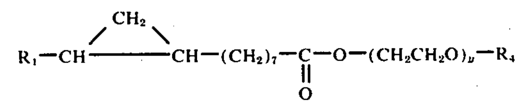 in which $R_1$ represents either a straight-chain alkyl or a straight-chain alkyl group interrupted by one or more cyclopropyl groups; $R_4$ is a lower alkyl group; and $y$ is an integer from 1 to 5.

The membrane mobility agents of the invention may be used to alter the mobility of membrane components in animal and plant cells to biologically alter such cells in the response to external stimuli. By way of illustration, the membrane mobility agents of the invention may be used (a) to alter the immunological response of lympocytes and thus stimulate antibody production; (b) to alter the pharmacological response of target cells in which pharmacologically responsive cells will be treated with the particular pharmacologically active compound together with the membrane mobility agent; (c) to alter the biological properties of cancer cells changing their response to chemotherapeutic compounds or per se precluding the tendency of cancer cells to undergo agglomeration; and (d) to fuse two or more cells to create a new hybrid cell containing the genetic information from the fused cells, in which two or more genetically-dissimilar cells (either animal or plant cells) will be treated with the membrane mobility agent to fuse such genetically-dissimilar cells into a new hybrid cell.

CHARACTERIZATION OF MEMBRANE MOBILITY AGENTS

Molecules of membrane mobility agents of the invention consist of two parts, namely a hydrophobic chain with disorderpromoting substituents, and a hydrophilic chain which bridges the gap between the hydrocarbon and the outer regions of the membrane. The fluidity-promoting hydrophobic chain in natural membranes is an unsaturated fatty acid, but these are subject to auto oxidation. Conversion of double bonds to cyclopropane rings by the Simmons-Smith reaction [Simmons et al. *J. Amer. Chem. Soc.*, 81, 4256–4264 (1969] removes the oxygen sensitivity [Kornberg et al., *Proc. Natl. Acad. Sci. U.S.*, 68, 2564–2568 (1971)] and preserves approximately the disorder-promoting geometry of the double bond.

Interesting, the unsaturated fatty acids present in the membranes of rapidly growing *Escherichia coli* cells are replaced to a considerable extent by cyclopropane acids after rapid growth has ceased [Cronan et al, *Biochim, Biophys. Acta*, 265, 29 (1972)]. However, we have observed that by themselves, these cyclopropane fatty acids are not membrane mobility agents since they lack a hydrophilic chain capable bridging the gap between the hydrocarbon and the outer regions of the membrane.

PREPARATION OF MEMBRANE MOBILITY AGENTS

Six active membrane mobility agents in accordance with the invention were synthesized by straight-forward chemical reactions and are described in Table I. The first three compounds (abbreviated $A_1C$, $A_2C$ and $A_3C$) were esters of 8-(2-n-octylcyclopropyl)-octanoic acid which, in turn, was prepared by the Simmons-Smith reaction with methyl oleate. The cyclopropane fatty acid was obtained and was then separately esterified with 2-methoxyethanol (to form $A_1C$), with 2-(2-methoxy)-ethoxyethanol (to form $A_2C$) and with 2-[2-(2-methoxy)-ethoxy] ethoxyethanol (to form $A_3C$), using conventional esterification techniques such as via the acyl chloride, or via the mixed anhydride with trifluoroacetic acid, or via the carbodiimide method.

The fourth compound ($A_2C_2$) was the 2-(2-methoxy)-ethoxyethyl ester of 8-[2-(2-n-pentylcyclopropylmethyl-cyclopropyl]-octanoic acid which, in turn, was prepared from the corresponding methyl ester produced by the Simmons-Smith reaction with methyl linoleate. The fifth compound was the 2-(2-methoxy)-ethoxyethyl ester of 8-(2-[2-(2-ethylcyclopropylmethyl)-cyclopropylmethyl]-cyclopropyl)-octanoic acid which, in turn was made from corresponding methyl ester produced from the Simmons-Smith reaction with methyl linolenate.

The sixth compound ($A_2CE$) was produced by reducing the methyl ester of 8-(2-n-octylcyclopropyl)-octanoic acid with lithium aluminum hydride to form the corresponding cyclopropane fatty alcohol which, in turn, was converted into the methane sulfonate which was then reacted with potassium 2-(2-methoxy)-ethoxyethoxide.

All six membrane mobility agents were carefully purified by chromatography. The compounds contained no detectable carbon-carbon double bonds when examined by NMR. Criteria for purity were: thin-layer chromatography (single spot), gas-liquid chromatography (>97% pure), infrared and NMR spectra, in agreement with structures.

The six membrane mobility agents were tested against the five additional (and inactive) compounds listed in Table I each of which possessed the same criteria for purity.

DEMONSTRATION OF BIOLOGICAL ACTIVITY

FIG. 1 summarizes the viability of lymphocytes treated with the membrane mobility agents $A_1C$, $A_2C$ and $A_3C$ compared to the inactive compound $A_2S$. In each of these tests, lymphocyte suspensions were incubated with the agents for 60 minutes. The viability of the cells thus incubated was evaluated by the dye-exclusion test, using trypan blue. As shown in FIG. 1, cytotoxicity measurements on lymphocytes with these compounds indicated a considerable dependence of toxicity on structure. Certain compounds, such as $A_2C$, were toxic at concentrations considerably above that at which maximum effect on mobility was observed. Some compounds (e.g., $A_3C$) showed toxicity with amounts close to that at which an effect on mobility was seen.

Cap formation was followed on rabbit lymphocytes preincubated for various periods of time with one of the compounds, then treated with fluorescent antibody. At least 20 minutes preincubation with the aqueous dispersion of agent $A_2C$ were required to produce a change in the observed rate from that of the control and between 1 and 2 h incubation was required for maximum response. A 1-h period was utilized in most experiments.

Figure 2:
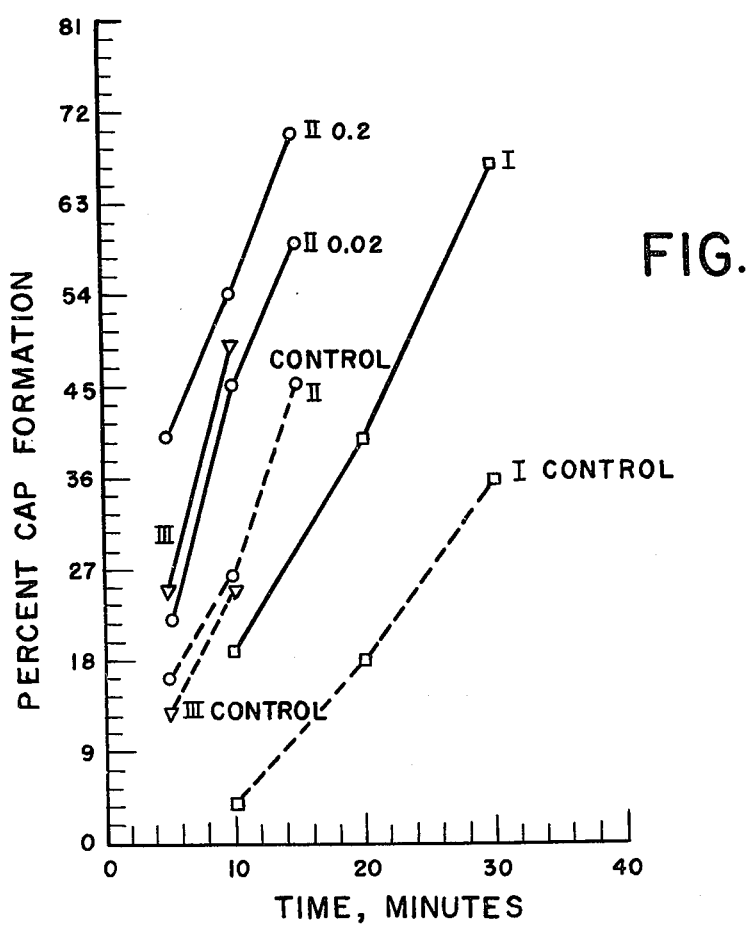

FIG. 2 illustrates the rate of cap formation in lymphocytes treated with $A_2C$. In each of these experiments rabbit blood was anticoagulated with heparin (200 I.U./cm$^3$) and diluted with NaCl-phosphate buffer, pH 7.3 (137 mM NaCl-1.8 mM $KH_2PO_4$-8.2 mM $Na_2HPO_4$) to 40% of original volume. Diluted blood was layered over sodium metrizoate (Nyegaard, Oslo, Norway)-Ficoll (Pharmacia, Uppsala, Sweden) mixture (containing 6.3% Ficoll and 10% sodium metrizoate), and centrifuged for 30 min. at 400 g at 25° C. Cells collected from the interphase contained over 80% lymphocytes. Cells were centrifuged, washed 3 times in buffer containing albumin and resuspended in the same or $A_2C$ buffer. ($A_2C$ was suspended in buffer (with Vortex) and albumin added). Final concentrations: lymphocytes 10$^7$ cells/cm$^3$. $A_2C$ 0.02–0.2 μl/cm$^3$, 0.2% albumin, 5 mM glucose. Usual sample volume: 0.2 cm$^3$. The cell suspension was incubated at 22° or 24° C for 60 min. Fluorescein-labeled goat anti-rabbit Ig antibodies (source: rabbit IgG injected into goat. Ig purified from antiserum by affinity chromatography on rabbit

TABLE I

MEMBRANE MOBILITY AGENTS

| Abbreviation | Formula | Systematic name |
|---|---|---|
| Active Compounds: | | |
| $A_1C$ | $CH_3(CH_2)_7\Delta(CH_2)_7COOCH_2CH_2OCH_3$ | 2-methoxyethyl 8-(2-n-octylcyclopropyl)-octanoate |
| $A_2C$ | $CH_3(CH_2)_7\Delta(CH_2)_7COOCH_2CH_2OCH_2CH_2OCH_3$ | 2-(2-methoxy)-ethoxyethyl 8-(2-n-octylcyclopropyl octanoate |
| $A_3C$ | $CH_3(CH_2)_7\Delta(CH_2)_7COOCH_2CH_2OCH_2CH_2OCH_2CH_2OCH_3$ | 2-[2-(2-methoxy)-ethoxy]ethoxyethyl 8-(2-n-octycyclopropyl)-octanoate |
| $A_2C_2$ | $CH_3(CH_2)_4\Delta CH_2\Delta(CH_2)_7COOCH_2CH_2OCH_2CH_2OCH_3$ | 2-(2-methoxy)-ethoxyethyl-8-[2-(2-n-pentylcyclopropylmethyl)-cyclopropyl]-octanoate |
| $A_2C_3$ | $CH_3CH_2\Delta CH_2\Delta CH_2\Delta(CH_2)_7COOCH_2CH_2OCH_2CH_2OCH_3$ | 2-(2-methoxy)-ethoxyethyl 8-(2-[2-(2-ethylcyclopropylmethyl)-cyclopropylmethyl]-cyclopropyl)-octanoate |
| $A_2CE$ | $CH_3(CH_2)_7\Delta(CH_2)_7CH_2OCH_2CH_2OCH_2CH_2OCH_3$ | 2-(2-methoxy)-ethoxyethyl 8-(2-n-octylcyclopropyl)-n-octyl ether |
| Inactive Compounds: | | |
| $A_2S$ | $CH_3(CH_2)_{16}COOCH_2CH_2OCH_2CH_2OCH_3$ | 2-(2-methoxy)-ethoxyethyl octadecanoate |
| MC | $CH_3(CH_2)_7\Delta(CH_2)_7COOCH_3$ | methyl 8-(2-n-octylcyclopropyl)-octanoate |
| $C_2$ | $CH_3(CH_2)_4\Delta CH_2\Delta(CH_2)_7COOH$ | 8-[2-(2-n-pentylcyclopropylmethyl-cyclopropyl]-octanoic acid |
| $A_2$ | $CH_3OCH_2CH_2OCH_2CH_2OH$ | 2-(2-methoxy)-ethoxyethanol |
| $A_1Hex$ | $CH_3(CH_2)_4COOCH_2CH_2OCH_3$ | 2-methoxyethyl hexanoate |

IgG-sepharose 4B, and conjugated with fluorescein isothiocyanate were then added to cells (0.05 mg per 2 × 10⁶ cells) and incubation continued. Samples were treated at intervals with cold 10 mM NaN$_3$ in buffer albumin, cells centrifuged and washed with same buffer, suspended in buffered glycerol and counted under a Zeiss fluorescence microscope. Three separate experiments are shown to illustrate the differences observed between control cells exhibiting various rates of cap formation and A$_2$C-treated cells. Expt I: 0.1 1 A$_2$C per cm$^3$; (log concn −3.7); temp. 22 C. Expt II: 0.02 and 0.2 A$_2$C per cm$^3$; temp. 24° C. Expt III: 0.2 A$_2$C per cm$^3$; temp. 24° C.

The rate of cap formation for cells treated with A$_2$C is compared with that of the corresponding controls in FIG. 2. Two points should be noted. First, the rate of cap formation in the treated cells is as much as 50% higher than that of the controls. Second, extrapolation to zero cap formation time reveals that the treated cells might be initially more "prepared" to form caps than the control cells. The mobility agent may affect the first stage of cluster formation as well as the subsequent cluster movement to result in caps. As shown by FIG. 2, inherent "high" or "low" capacity for cap formation does not alter the effects produced by the mobility agent.

The effects of most of the compounds listed in Table I were examined after a standard incubation period. Considerable variation in effectiveness as a membrane mobility agent was observed. Of the hydrophilic chains, A$_2$(CH$_3$OCH$_2$CH$_2$OCH$_2$CH$_2$) gave rise to compounds with the highest activity.

Figure 3:
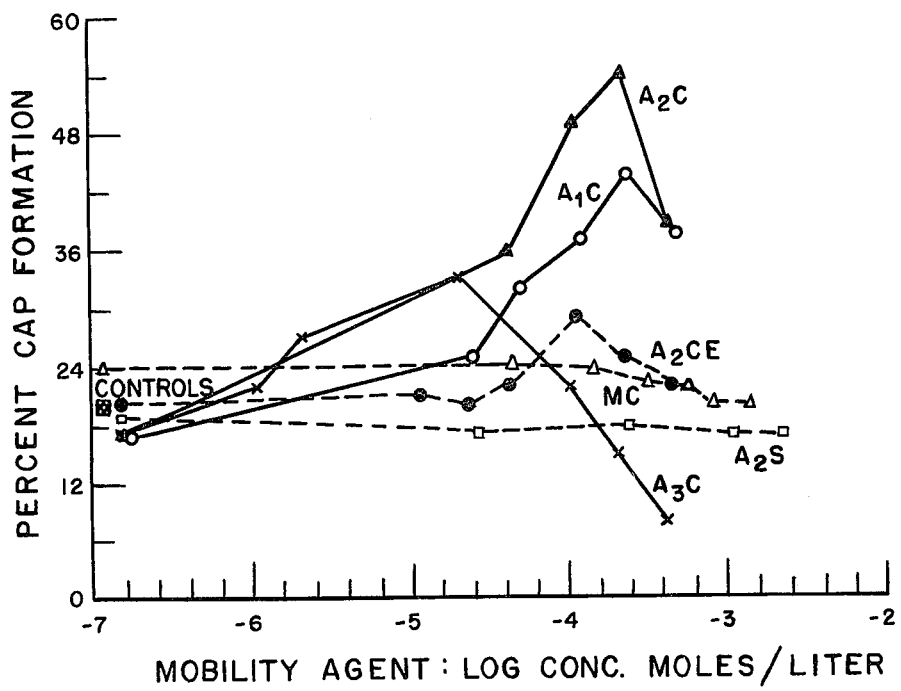
Figure 4:
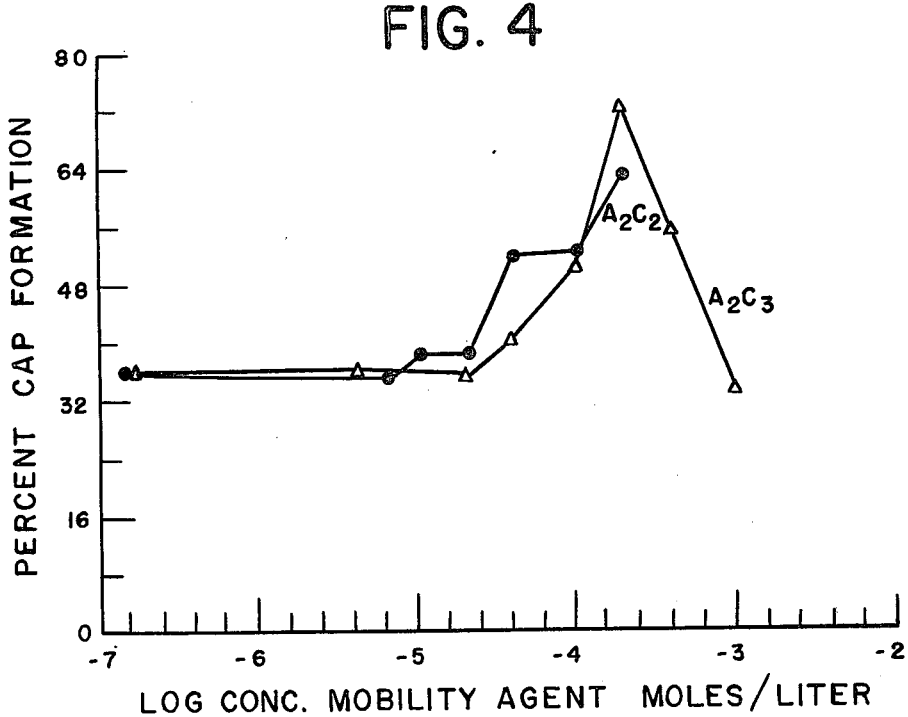

Cap formation after treatment with the CH$_3$, A$_1$, A$_2$ and A$_3$ esters of the C acid is illustrated in FIG. 3. One, two or three cyclopropane rings at the hydrocarbon end of the hydrophobic C$_{18}$ chain do not differ greatly in effect on agent activity, which is illustrated in FIG. 4. The ether, A$_2$CE, was less than the ester A$_1$C in effect. Other compounds listed in Table I exhibited little or no effect on cap formation.

UTILIZATION OF MEMBRANE MOBILITY AGENTS

The membrane mobility agents of the invention can be utilized to alter in a useful way the biological responses of systems in which the membrane of the cell is involved. Several examples are described below:

A. Immunological Behavior of Lymphocytes

Lymphocytes are central to the immunological response of mammalian systems. Cap formation, which results from the interaction of an antigenic site in the cell membrane with an antibody, reflects the response of the lymphocytes to situations in which an immunological response of the organism might be required. The membrane mobility agents of the invention (1) increase the rate of cap formation, (2) increase the extent of cap formation within a specified period of time (cf/FIGS. 2 to 4) or, put another way, increase the rate in which lymphocytes respond to immunological stimuli. As a consequence, these agents are useful in the same sense as adjuvants useful in many situations in which it may be desirable to promote the immunological response of organisms. By way of illustration, the membrane mobility agents of the invention can be used to increase the rate of antibody production to antigens in such animals as horse, goat, rabbit or other such animals as are used in the production of antibodies for diagnostic and therapeutic purposes. Similarly, theses compounds can be used to increase the antibody response in individuals afflicted with infectious or malignant diseases.

B. Fusion of Cells

Fusion of animal cells have proven very useful in the scientific study of such cells. The need for new plant varieties is well known, for the purpose of combining and enhancing useful characters in a single plant which can be grown all over the world. Usual techniques of plant hybridization are very slow, and not suitable for plants of dissimilar species. Methods of hybridizing plant cells would be extremely useful.

The membrane mobility agents of the invention have been shown to cause the fusion of hen red blood cells by treatment according to the following procedure:

Blood from the brachial vein of adult hens was mixed with heparin (as anticoagulant), centrifuged and the buffy coat removed. The erythrocytes were washed twice with 150 mM NaCl and once with buffer containing 76 mM sodium acetate, 70 mM NaCl, 1 mM CaCl$_2$ and 100 mg/cc Dextran (MW 70,000) Pharmacia, Uppsala, Sweden (pH 5.7). The buffer is similar to but simpler than that used in a similar procedure by Lucy et al. The cells were resuspended in the same buffer and mixed with an equal volume of a suspension of the mobility agent A$_2$C dispersed in 150 mM NaCl by sonication. (ca. 2 min.) No special precautions are required during sonication and the suspension remains active for several hours. The final concentrations of A$_2$C used ranged between 0.06μl to 0.5 μl/cc containing 2-3 × 10⁸ cells, 0.5 mM CaCl$_2$, 38 mM sodium acetate, 110 mM NaCl and dextran (50 mg/cc). Cell suspensions were incubated at the desired temperature, mixed gently every 5 – 15 minutes and aliquots removed at intervals for viewing and photography at room temperature. Addition of A$_2$C in amounts of 0.125 to 0.5 μl/cc of cell suspension led to rounding and swelling of the cells within 10 – 30 minutes after mixing and incubation at 37° C. Contacts between the rounded and swollen cells were noted, followed by increasing degrees of fusion, starting with binucleated, trinucleated and tetranucleated cells and proceeding to multinucleated cells. The fusion process eventually involved most of the erythrocytes.

Accordingly, the membrane mobility agents of the invention can be used in (1) hybridization of plant cells, combining cells of different genetic constitution, so as to create new plants, and (2), diagnosis of genetic diseases, in cases in which hybridization of an unknown cell with a known cell may reveal and locate the genetic problem.

C. Fusion of Cells and Vesicles

The introduction of various materials into a cell is often desirable and useful, e.g., introduction of poorly soluble drugs, or of genetic material, or of materials which have undesirable activity outside of the cell, but which are useful within the cell, such as missing enzymes.

The membrane mobility agents of the invention can be useful in aiding the introduction of vesicles containing the desired agents into cells, by aiding in the process of fusion. Vesicles are suspensions of phospholipids prepared by sonication of such materials as lecithin in the presence of the desired agent.

D. Pharmacological Activity of Drugs

The pharmacological activity of many drugs could be raised if their rate of entry into the cell could be promoted. The entry of pharmacological agents, such as certain diazene derivatives like DIP [diazene dicarboxylic acid bis(N'-methylpiperazide)] which oxidizes the glutathione within cells to glutathione disulfide, is augmented by the addition of membrane mobility agents of the invention to such cells as red blood cells.

Based on these observations, the activity of many drugs (e.g., antibiotics, insecticides, herbicides, etc.) will be increased by the use of the membrane mobility agents of the invention.

E. Augmentation of Release from Cells

Many intracellular agents are released from cells at rates which are below that desirable for optimum biological activity. In recent experiments, we have observed that neurotransmitter release is augmented by a small factor through the use of such agents as $A_2C$, from which data we expect that many other release processes can be augmented. For example, the use of the membrane mobility agents of the invention on brain tissue would lead to more efficient response to pharmacologically-active compounds and stimuli (such as electrical stimuli) on such brain tissue.

Another example exists in lung surfactant release. Insufficient surfactant in the baby's lung is the major manifestation of hyaline membrane disease. The use of the membrane mobility agents such as those described herein are expected to be useful in promoting release of the surfactant in a therapeutically meaningful way.

F. Alteration in Membranes of Malignant Cells

Some malignant cells, like mastocytoma, agglutinate in the presence of wheat germ agglutinin. Treatment of the cells with the membrane mobility agent $A_2C$ has been found to cause caps to form and to diminish the extent of agglutination, causing such cancer cells to behave similarly to normal cells.

We claim:

1. Compounds capable of functioning as membrane mobility agents in plant and animal cells and having a structure represented by the formula

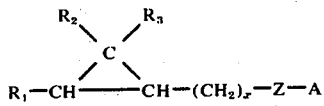

in which A represents a polyalkoxyalkyl hydrophilic chain; Z represents an ester linkage

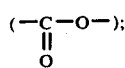

$R_1$ represents a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

2. Membrane mobility agents according to claim 1, in which Z represents an ester linkage.

3. Membrane mobility agents according to claim 1, in which the hydrophilic chain A is an $\omega$-alkoxypolyethoxyethyl group.

4. Membrane mobility agents according to claim 1, in which the membrane mobility agent is a cyclopropane fatty acid ester having a structure represented by the formula

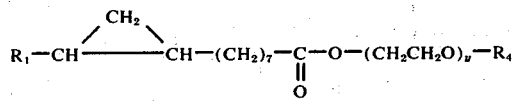

in which $R_1$ represents either a straight-chain alkyl or a straight-chain alkyl group interrupted by one or more cyclopropyl groups; $R_4$ is a lower alkyl group; and $y$ is an interger from 1 to 5.

5. Membrane mobility agents according to claim 4, in which $R_1$ is a n-octyl group; $R_4$ is a methyl group; and $y$ is an integer from 1 to 3.

6. 2-(2-Methoxy)-ethoxyethyl 8-(2-n-octylcyclopropyl)-octanoate.

7. A method for altering the mobility of membrane components in animal and plant cells to biologically alter such cells in their response to external stimuli which comprises treating such cells with an effective amount of at least one compound having a structure represented by the formula

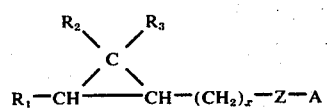

in which A represents a polyalkoxyalkyl hydrophilic chain; Z represents an ester linkage

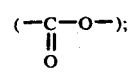

$R_1$ represents either a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

8. A method for altering the mobility of membrane components in animal and plant cells to biologically alter such cells in their response to external stimuli according to claim 7, in which the membrane mobility agent is a cyclopropane fatty acid ester having a structure represented by the formula

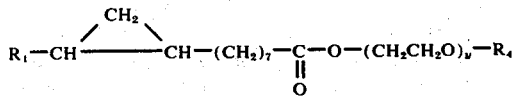

in which $R_1$ represents either a straight-chain alkyl or a straight-chain alkyl group interrupted by one or more cyclopropyl groups; $R_4$ is a lower alkyl group; and $y$ is an integer from 1 to 5.

9. A method for altering the immunological response of lymphocytes which comprises treating lymphocyte cells with an effective amount of at least one membrane mobility agent having a structure represented by the formula

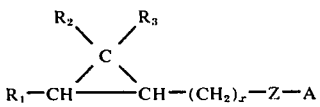

in which A represents a polyalkoxyalkyl hydrophilic chain; Z represents an ester linkage

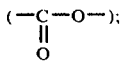

$R_1$ represents either a straight-chain alkyl group or a straight-chain alkyl group interrupted by one or more cycloropyl groups; $R_2$ and $R_3$ each represent either hydrogen, lower alkyl, or a halogen group; and $x$ represents an integer from 2 to 10.

10. A method for altering the immunological response of lymphocytes according to claim 9, in which the membrane mobility agent is a cyclopropane fatty acid ester having a structure represented by the formula

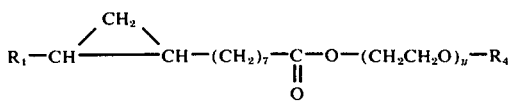

in which $R_1$ represents either a straight-chain alkyl or a straight-chain alkyl group interrupted by one or more cyclopropyl groups; $R_4$ is a lower alkyl group; and $y$ is an integer from 1 to 5.

11. A method for altering the pharmacological response of target cells which comprises treating such cells with effective amounts of (a) a pharmacologically-active compound to which such cells are responsive, and (b) at least one membrane mobility agent having a structure represented by the formula

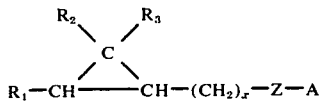

in which A represents a polyalkoxyalkyl hydrophilic chain; Z represents an ester linkage

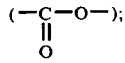

$R_1$ represents a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

12. A method for altering the pharmacological response of target cells according to claim 11, in which the membrane mobility agent is a cyclopropane fatty acid ester having a structure represented by the formula

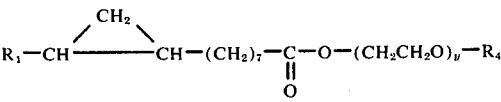

in which $R_1$ represents either a straight-chain alkyl or a straight-chain alkyl group interrupted by one or more cyclopropyl groups; $R_4$ is a lower alkyl group; and $y$ is an integer from 1 to 5.

13. A method for altering the biological properties of cancer cells which comprises treating cancer cells with an effective amount of at least one membrane mobility agent having a structure represented by the formula

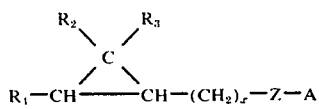

in which A represents a polyalkoxyalkyl hydrophilic chain; Z represents an ester linkage

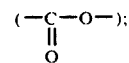

$R_1$ represents either a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

14. A method for altering the biological properties of cancer cells according to claim 13, in which the membrane mobility agent is a cyclopropane fatty acid ester having a structure represented by the formula

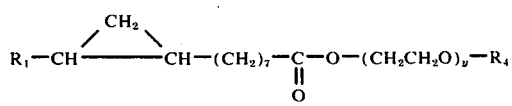

in which $R_1$ represents either a straight-chain alkyl or a straight-chain alkyl group interrupted by one or more cyclopropyl groups; $R_4$ is a lower alkyl group; and $y$ is an integer from 1 to 5.

15. A method for fusing two or more cells to create a new hybrid cell containing the genetic information from the fused cells which comprises treating two or more genetically-dissimilar cells with an effective amount of at least one membrane mobility agent to fuse such genetically-dissimilar cells into a new hybrid cell containing the genetic information from the fused cells, the membrane mobility agent having a structure represented by the formula

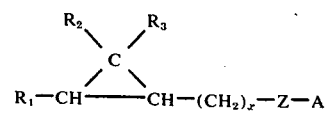

in which A represents a polyalkoxyalkyl hydrophilic chain; Z represents an ester linkage

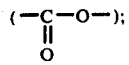

$R_1$ represents either a straight-chain alkyl group or a straight-chain alkyl group interrupted by one or more cyclopropyl groups; $R_2$ and $R_3$ each represent either hydrogen, lower alkyl, or a halogen group; and $x$ represents an integer from 2 to 10.

16. A method for fusing two or more cells to create a new hybrid cell containing the genetic information from the fused cells according to claim 15, in which the membrane mobility agent is a cyclopropane fatty acid ester haviing a structure represented by the formula

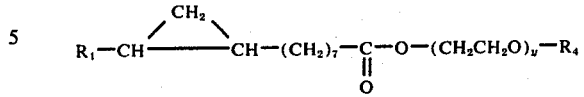

in which $R_1$ represents either a straight-chain alkyl group or a straight-chain alkyl group interrupted by one or more cyclopropyl groups; $R_4$ is a lower alkyl group; and $y$ is an integer from 1 to 5.

* * * * *